(12) United States Patent
Kraft-Kivikoski

(10) Patent No.: US 6,402,714 B1
(45) Date of Patent: Jun. 11, 2002

(54) APPARATUS AND METHOD FOR CONTROLLING HIGH FLOW INSUFFLATION

(75) Inventor: Juergen Kraft-Kivikoski, Radolfzell (DE)

(73) Assignee: Karl Storz GmbH & Co., KG (DE)

( * ) Notice: Subject to any disclaimer, the term of this patent is extended or adjusted under 35 U.S.C. 154(b) by 0 days.

(21) Appl. No.: 09/438,902

(22) Filed: Nov. 12, 1999

(51) Int. Cl.$^7$ .............................................. A61M 37/00
(52) U.S. Cl. ......................................... 604/23; 600/560
(58) Field of Search .............................. 604/23, 26, 27, 604/28, 500, 118, 119; 600/560

(56) References Cited

U.S. PATENT DOCUMENTS

| | | | |
|---|---|---|---|
| 4,048,992 A | | 9/1977 | Lindemann et al. |
| 4,207,887 A | | 6/1980 | Hiltebrandt et al. |
| 4,676,774 A | | 6/1987 | Semm et al. |
| 4,681,563 A | * | 7/1987 | Deckert et al. |
| 4,715,372 A | | 12/1987 | Philippbar et al. |
| 4,735,606 A | * | 4/1988 | Davison |
| 4,874,362 A | | 10/1989 | Wiest et al. |
| 4,878,894 A | * | 11/1989 | Sutter, Jr. et al. |
| 5,006,109 A | | 4/1991 | Douglas et al. |
| 5,019,037 A | * | 5/1991 | Wang et al. |
| 5,066,276 A | * | 11/1991 | Wang |
| 5,360,396 A | | 11/1994 | Chan |
| 5,439,441 A | | 8/1995 | Grimsley et al. |
| 5,690,831 A | * | 11/1997 | Kenley et al. |
| 5,800,381 A | | 9/1998 | Ognier |
| 5,989,238 A | * | 11/1999 | Ginsburg |
| 6,068,609 A | * | 5/2000 | Ott et al. |
| 6,126,657 A | * | 10/2000 | Edwards et al. |
| 6,196,222 B1 | * | 3/2001 | Heinonen et al. |

* cited by examiner

Primary Examiner—Brian L. Casler
Assistant Examiner—Kevin C. Sirmons
(74) Attorney, Agent, or Firm—St. Onge Steward Johnston & Reens LLC

(57) ABSTRACT

A pulsed insulation system for administering an insufflation procedure includes a controller programmed to have a multi-mode operation. The controller switches the insufflation system to adjust an insufflation pressure to a nominal value in a first mode of operation of the controller. Upon encountering an obstruction by a Veress needle, the controller switches the insufflation system in a second mode, so as to adjust the insufflation pressure to a maximum target value and to have an interruption phase of pulse controllably increased. The interruption phase of pulse in the second mode is extended so as to enable a pressurized fluid accumulated at an upstream end of the Veress needle to dissipate therethrough before a measurement of the intracavity pressure is made.

32 Claims, 10 Drawing Sheets

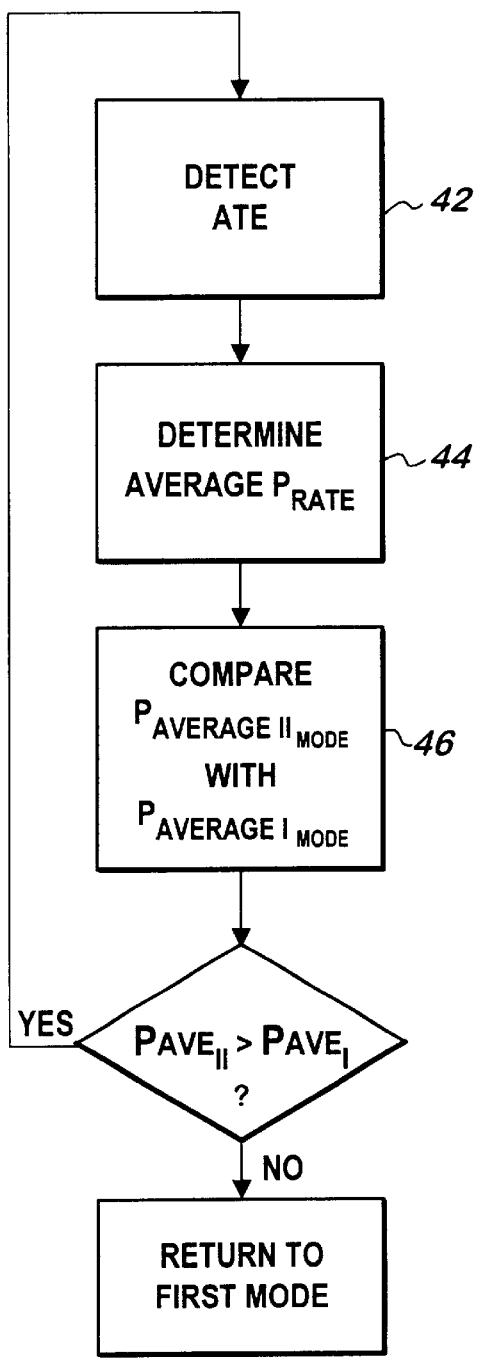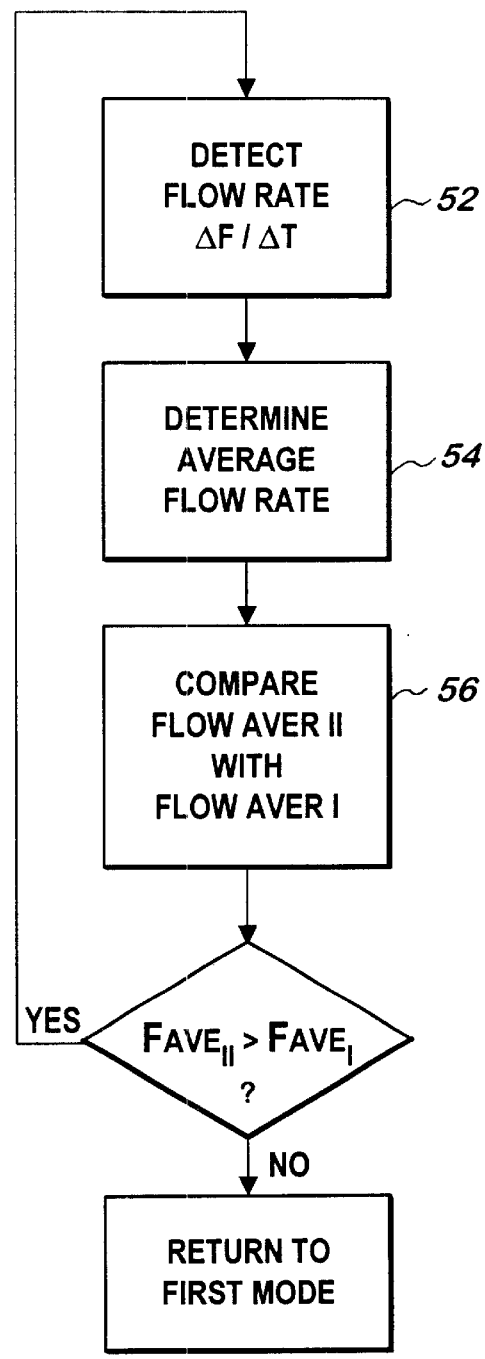
*FIG. 13*  *FIG. 14*

APPARATUS AND METHOD FOR CONTROLLING HIGH FLOW INSUFFLATION

FIELD OF THE INVENTION

The present invention relates to an insufflation apparatus improving the accuracy, safety and speed of insufflation of fluid into a human or animal body. Particularly, the invention relates to an apparatus adapted to regulate the pressure inside a body cavity by controllably increasing an interruption phase of an insufflation pulse upon identifying obstructions encountered by a Veress needle during and after its penetration into the body cavity.

BACKGROUND OF THE INVENTION

Surgical procedures require the insufflation of fluid into a body cavity. Known insufflation apparatuses pass a fluid from the pressurized reservoir through the fluid line and an insufflation or Veress needle into the body cavity required to be maintained at a certain pressure.

The pressure to be regulated is the pressure of the patient, however, the pressure sensors are found inside the apparatus and measure the insufflation pressure upstream of an insufflation needle penetrating a patient's body. Both pressures are only equal if no gas is flowing through the needle. This is the reason that electronic insufflators do not fill the operation area continually, but only in phases. A combination of a filling phase and an interruption phase during which the gas flow is constantly brought back to zero in order to measure the pressure of the patient constitutes a pulse.

U.S. Pat. No. 4,048,992 to Lindemann et al., discloses a pressure gauge reading a back pressure of insufflated gas built up with the predetermined insufflated gas volume upstream of a Veress needle. As time passes, the pressure differential across the needle becomes equal to zero as indicated by a zero flow rate on a flow gauge, thus making a user assume that the pressure inside a cavity is equal to the back pressure.

U.S. Pat. No. 4,676,774 to Semm et al., discloses an apparatus for the insufflation of gas into a body cavity and including a pressure gauge, whose measured value is fed as a function of time into an electronic evaluation circuit and is converted into the intraabdominal pressure. Such measurement is based on the experience that shortly after the start of insufflation, steady-state conditions occur so that the measured value of the pressure gauge is approximately constant. Since the measured value of the pressure gauge is time differentiated, the first derivative is equal to zero and corresponds to the insignificant intraabdominal overpressure built up in the cavity. Thus, the pressure on the pressure gauge upstream of the insufflator indicates the insufflator's flow resistance and is constant. In order to calculate the static intraabdominal pressure the pressure at the start of insufflation has to be subtracted from the measured rising pressure.

U.S. Pat. No. 4,715,372 to Philippbar et al., discloses a gas insufflation apparatus for use in an arthroscopic attachment for a laser system in order to distend a joint during arthroscopic surgery. The apparatus includes a first regulator insufflating the gas directly into the knee joint at a minimal pressure and a second regulator applying the gas at a maximum pressure into an arthroscopic attachment.

U.S. Pat. No. 5,006,109 to Douglas et al., teaches a system for administering gas to a patient during an endoscopic procedure. The system includes a pressure regulator and a volumetric gas flow regulator continuously reflecting the pressure and flow rate of the gas which allow the user to modify these parameters during the procedure.

U.S. Pat. No. 5,360,396 to Chan discloses an apparatus for insufflation of a body cavity including a pressure reliever that allows the insufflating gas to escape if the pressure at the exit of a pressure reducer exceeds a predetermined pressure.

U.S. Pat. No. 5,439,441 discloses an insufflation device having a regulating device that is programmed to process and to store pressure reading values in the body cavity during each pause phase at which the introduction of gas into a body cavity to be inflated is discontinued. These readings are taken at plural, discrete intervals of time. The difference between a predetermined number of the most recent pressure reading values are compared to determined the pressure differential between highest and lowest pressure reading values. A series of results indicating that this pressure differential is less than a predetermined value determines that the pressure in the body has stabilized and equal to the pressure upstream of a needle inserted in the cavity.

U.S. Pat. No. 4,874,362 to Weist discloses a device and method for continuous insufflation wherein the intra-abdominal pressure is measured at an end of each cycle when a flow rate of gas is indicated to be zero. The rate is brought down to this value by controlling a pressure reducer that electrically connected with a CPU and whose working mode is a function of a clock generator and a nominal pressure generator. Particularly, the pressure reducer valve operates in two different modes. The first mode is characterized by maintaining a nominal pressure if a flow rate does not exceed a preset value. The pressure reducer is switched to the second mode, wherein an output pressure of the reducer is increased to a maximum insufflation value if the flow rate exceeds the preset value. The device disclosed in this reference operates without taking into consideration certain factors negatively affecting measurements of the intraabdominal pressure, for example, presence of gas flow through a Veress needle while a flow rate gage clearly indicates its absence.

All of the above disclosed devices are based on the premise that when an internal apparatus gas flow is brought back to zero at the end of a filling phase, no gas flows through a Veress needle into a body cavity thereby allowing correct determination of the intracavity pressure. During a surgical insufflation procedure of FIG. 1, an insufflation pressure $P_{ins}$ is shown to decay through a Veress needle in a relatively abrupt manner upon terminating a filling phase. Upon indicating a zero flow rate upstream of the Veress needle by a flow rate gauge, an equalization state between the insufflation pressure and an intracavity pressure $P_{abd}$ is presumed to be reached and the intracavity pressure is measured within the interruption phase $T_i = T_c - T_p$ of the pulse.

However, in many instances gas still flows through the Veress needle upon the presumed balance between the insufflation and intracavity pressures, thereby rendering the result of determination to be erroneous, as shown in dash lines in FIG. 1. The rational behind this phenomenon is the accumulation of gas at the upstream end of the Veress needle during a filling phase.

Typically, this is a result of obstructions encountered by the Veress needle during a surgery. For instance, during the pneumo-peritoneum penetration the needle may encounter the skin, the intra-abdominal wall, muscles. Each of these parts of a body adds to the dead volume of fluid that may eventually render the measurement of intracavity pressure dangerously low compared to an actual value.

Further, a modern high flow insufflator is capable of producing a gas flow rate up to 30 l/min that might be necessary in some surgical procedures at a phase when the intracavity pressure has stabilized. Many practitioners, knowing a desirable rate of gas flow, set a high target value at the start of insufflation. However, since the opening of the Veress needle allows only a low gas flow, usually not exceeding 2–2.5 l/min, the dead volume in front of the Veress needle is "filled" with the maximum insufflation pressure. On completion of the filler phase, if the apparatus reduces the gas flow back to zero in order to measure the intracavity pressure, then there is still a pressure differential between the upstream and downstream ends of the needle. This dead volume decays through the needle into the cavity. Thus, although an internal apparatus gas flow is equal to zero, in fact gas flows from the dead volume in to the patient making measurements of the intracavity pressure erroneous.

Those flow conditions in the interior of the body in the immediate vicinity of the Veress needle are different during each insertion and further contribute to the inaccuracy of these measurements. Moreover, the complete line system including pressure reduces, moisturizes, heaters, and so on, differs between the individual operations thereby adding to the margin of error of the indicated pressure value.

Thus, safety considerations necessitate a need for an insufflation apparatus and method for administering a pressurized fluid to a body cavity which provides accurate determination and control of the intracavity pressure during an interruption phase between pulses when there is no undetected gas flow through a Veress needle.

SUMMARY OF THE INVENTION

The foregoing problems are solved by an inventive insufflation apparatus, wherein an accurate measurement of intracavity pressure is achieved by increasing an interruption phase of an insufflation cycle upon detecting obstructions that may successively be encountered by a Veress needle and a trocar in a body cavity. As a consequence of an increased interruption phase, a volume of pressurized fluid accumulated at an upstream end of the Veress needle dissipates through the Veress needle before measuring the intracavity pressure. Thus, a pressure regulator is controllable as a function of detecting an obstruction and a nominal pressure generator.

The inventive insufflation apparatus having two modes of operation available during a filling phase achieves this. In the first mode, the internal apparatus pressure is adjusted toward a minimum target value, which is generally equal to a preset nominal pressure, if both, a measure flow rate and a measured pressure are at most equal to predetermined values. However, once an obstruction encountered by the Veress needle manifests itself by an abrupt pressure increase and by an abrupt flow rate drop, a control processing unit (CPU) electrically switches the pressure controller to the second mode. Particularly, the controller's output pressure defining an internal apparatus pressure is raised to its maximum (50 mmHg) for at least one insufflation cycle which is characterized by the increased interruption phase in accordance with this invention.

According to one aspect of the invention, the pressure controller is automatically switched to its second mode thereby increasing both, the internal apparatus pressure and, as a consequence, the dead volume upstream from the Veress needles. While the increased pressure helps overcome an obstruction, the dead volume needs an additional decay period of time that is automatically monitored by the CPU by controllably increasing the interruption phase and, as a consequence, the entire cycle. At the end of the interruption phase, the pressure gage correctly indicates an intracavity or intra-abdominal pressure. If, however, the obstruction persists, the next cycle is performed in accordance to the second mode of operation. Since this process is continuous, once the obstruction is overcome, the controller returns to its first normal mode of operation, so as the entire duration of the insufflation process is not significantly increased.

According to another aspect of the invention, in the first mode, the internal apparatus pressure is adjusted toward a minimum target value during the entire duration of a filling phase. However, if an obstruction encountered by the Veress needle is detected, the CPU of the insufflation apparatus is programmed to switch it to the second mode, wherein the internal apparatus pressure is increased to and maintained at a maximum value during only a portion of the filling phase. If the obstruction has not been yet passed through, then, upon termination of this portion of the filling phase, the controller interrupts the supply of pressurized fluid in the apparatus, thereby extending the interruption phase of pulse relative to the same interruption phase during the first mode. Thus, despite the fact that the dead volume in the second mode is greater than it is in the first mode, the duration of the interruption phase during the second mode is sufficient to allow the dead volume to empty itself before a measurement of an intracavity pressure is taken. However, according to this aspect of the invention, the cycle is not increased, and the entire duration of insufflation remains unchanged.

The insufflation apparatus according to the invention includes a gas supply system which has a pressurized gas storage reservoir, a pressure reduction valve, pressure and flow rate transducers coupled to the CPU, and a relief valve all connected to the gas supply line. An electronically operated pressure-regulating valve controllably blocking gas flow through the apparatus is responsive to the CPU for adjusting the pressure of fluid in the line within a 0–50 mmHg range. A cut-off electronically operated, which is in flow communication with the pressure-regulating valve, controllably switches the entire apparatus off upon expiration of the pre-set period.

In contrast to a typical feedback control that tends to bring a controlled value to the same preliminarily set target value, the method, in accordance with the invention, includes a step of setting a maximum target value at the time of detecting an obstruction. This is achieved, as previously described, by increasing the output signal of the electronic controller operating the pressure-regulated valve.

Upon detecting reestablishment of normal conditions, the insufflation apparatus returns to the first mode. Therefore, the apparatus and method in accordance with the invention provide an average gas flow during the entire duration of a surgical procedure and maintain substantially constant intracavity pressure regardless of obstructions encountered by the needle after the start of this procedure.

According to still another aspect of the invention, when the intracavity pressure has reached a nominal value, the Veress needle is replaced by a trocar having a large cross-section that allows the insufflator to operate at high flow rates. During this stage of operation, the most dangerous situation occurs when a leak is formed. Such leak may be, for example, a result of a faulty valve. Absent detection of the obstruction, a flow rate transducer visually indicates that a gas flow exceeds a preset flow rate, which automatically switches the apparatus in a third mode of operation monitored by the CPU. In contrast to the second mode of operation, this mode, while performed at an increased insufflation pressure, is characterized by a regular interruption phase, which is equal to the interruption phase of the first mode.

It is therefore an object of the invention to provide an insufflation apparatus maintaining safe administration of gas to a body cavity during an endoscopic procedure.

Another object of the invention is to provide an insufflation apparatus capable of monitoring precipitous variations in an internal apparatus gas flow and pressure signifying encounter of an obstruction by a Veress needle during its penetration into a body cavity.

A further object of the invention is to provide an insufflation apparatus adjusting its pressure in response to a precipitous variation in a measured intra-cavity pressure between nominal and maximum target values corresponding to first and second modes of operation of the insufflation apparatus.

Still another object of the invention is to provide an insufflation apparatus having an electronic controller automatically increasing both, an internal apparatus pressure and an interruption phase of the insufflation cycle.

A further object of the invention is to provide an insufflation apparatus controllably increasing an interruption phase and, as a consequence the entire duration of the cycle in response to detecting an obstruction.

Still another object of the invention is to provide an insufflation apparatus controllably increasing an interruption phase while decreasing a filling phase of the cycle so as to keep the total time of the cycle unchanged in response to detecting an obstruction.

Yet another object of the invention is to provide an insufflation apparatus having an electronic controller automatically adjusting an insufflation pressure in response to a precipitous increase in the measured gas flow above a preset flow rate.

Another object of the invention is to provide an electronic controller automatically determining duration of a filling phase and selectively switching the insufflation apparatus to a mode characterized by a maximum target value that is set in response to detecting obstructions encountered by a Veress needle.

A further object of the invention is to provide an insulation apparatus controllably increasing an internal apparatus pressure in response to a signal generated by a flow rate transducer that indicates a critical increase of the gas flow.

Still another object of the invention is to provide a method for measuring intracavity pressure, avoiding the inaccuracy of measuring during an endoscopic procedure.

Yet another object of the invention is to provide a method for measuring intracavity pressure in a pulsed manner and capable of detecting obstructions encountered by a Veress needle during penetration into a body cavity.

Another object of the invention is to provide a method for measuring intracavity pressure having two modes of operations characterized by different target values that are set in response to detection of obstructions encountered by a Veress needle.

Still another object of the invention is to provide a method for measuring intracavity pressure providing long decay periods for draining the dead volume of accumulated pressurized fluid without a perceptible reduction of the average gas flow.

While the following is shown and considered to be the preferred embodiment of the present invention, it will be obvious to those skilled in the art that various changes and modifications may be made therein without departing from the scope of the invention.

BRIEF DESCRIPTION OF THE DRAWINGS

The above and other objects, features and advantages will become more readily apparent from the following description of the preferred embodiment of the invention, as illustrated in the accompanying drawings, in which:

FIG. 13 is a flow diagram illustrating one of the embodiments of a controlling system according to the invention capable of switching between the second and first mode; and FIG. 14 is a flow diagram illustrating another embodiment of a controlling system capable of switching between the second and first mode in accordance with the invention.

DETAILED DESCRIPTION

Figure 1:
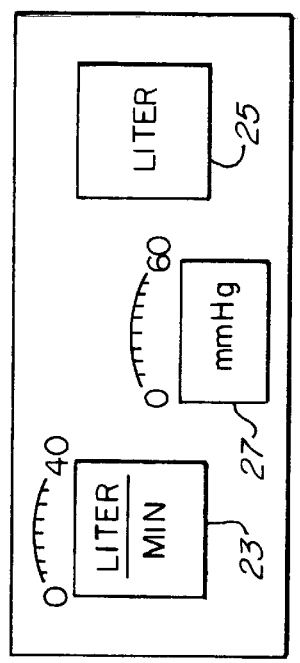
FIG. 1 is a timing diagram illustrating a process of measurement of an intracavity pressure in an insufflation surgical procedure according to the known Prior Art.
Figure 3:
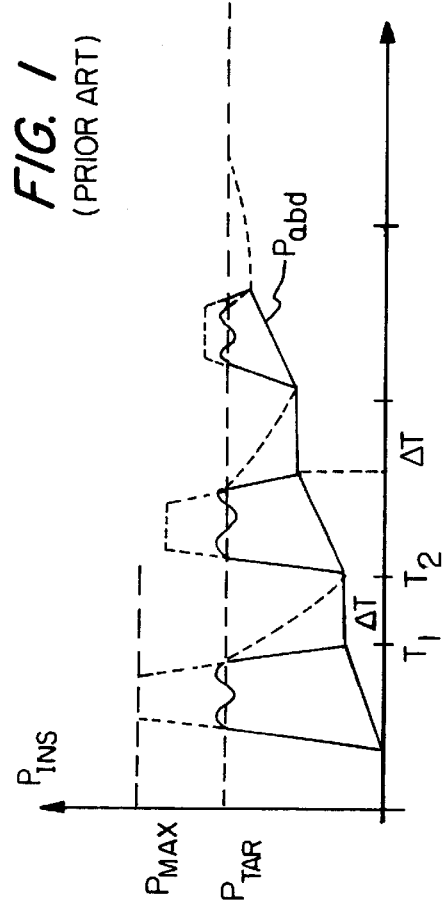
FIG. 3 is an elevational view of the front panel of the insufflator apparatus of FIG. 2.
Figure 2:
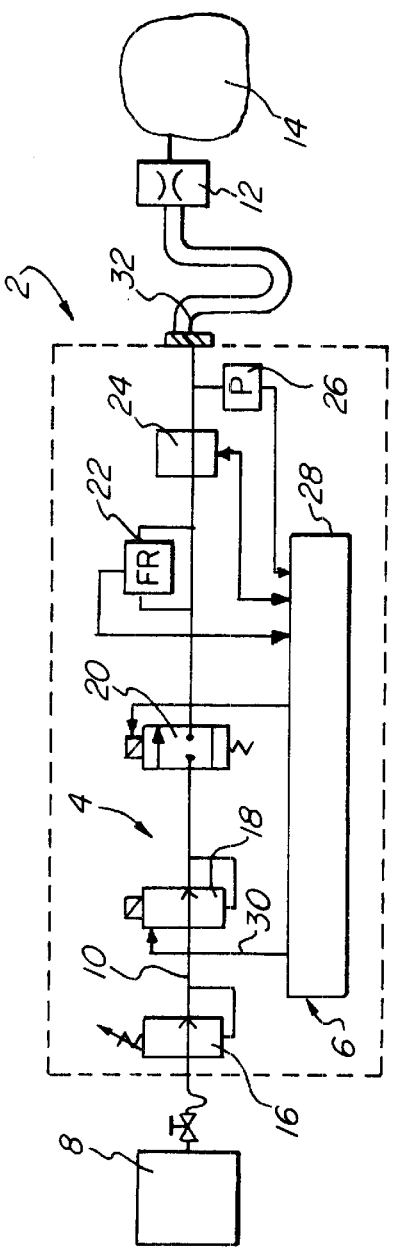
FIG. 2 is a schematic block diagram of an insufflation apparatus of the invention.

Referring to FIGS. 2–3, a schematic block diagram of an insufflation apparatus 2 of the invention includes a fluid supply system 4 and an electronic control system 6. The electronic control system 6 regulates the internal pressure $P_{ins}$ upstream of a Veress needle 12 in response to conditions undergone by this needle during its penetration into a body cavity 14. According to the invention, the control system is capable of detecting obstructions encountered by the Veress needle so as to switch the insufflation apparatus 2 between its different modes of operation in response to such detection, as will be explained herebelow.

Particularly, the fluid supply system 2 passes a pressurized fluid, which is typically $CO_2$ gas, from a reservoir 8 through a fluid line 10 and into the body cavity 14 via an insulator such as the Veress needle 12 positioned in flow communication with the body cavity 14. The reservoir 8, capable of storing the fluid pressurized up to 60 bar, is in flow communication via the fluid line 10 with a pressure reducer 16. This pressure reducer 16 lowers the high pressure of the reservoir down to, for example, 2 bar, and is connected in series with an electronic pressure regulator 18. The pressure regulator 18 incorporates an adjustable response to an electronic control signal to supply an insufflation pressure $P_{ins}$ ranging from 0 to 50 mmHg, thereby providing a continuous insufflation process. A cut-off solenoid valve 20 spaced downstream of the pressure regulator 18 is turned on at the beginning of the insufflation and is turned off at the end of the surgical procedure.

Further along a path of the pressurized fluid is a flow transducer 22 that provides an electronic signal proportional to flows of the pressurized fluid varying between 0 and 40 Standard Liters Per Minute (l/min). The outlet of the flow transducer 22 is connected to a relief valve 24 relieving pressures above 55 mmHg and a pressure transducer 26, which generates an electronic signal proportional to insufflation pressures $P_{ins}$.

A signal indicating the rate of flow per unit of time may be read on an electric flow indicator 23 having a graduated scale from 0 to 40 liters per minute. By means of an integrator (not shown), the total flow of pressurized fluid is determined and indicated on an electric indicator 25 having a scale graduated in liters. Knowledge of the total flow of fluid is necessary since if the insufflation apparatus or the body cavity allows pressurized fluid to leak, the measurement of the rate of flow cannot be indicative of the patient's condition. A pressure gauge 27 indicates the insulation pressure upstream of the Veress needle 12 and, at the times when the flow indicator 23 shows a zero flow rate (also, see FIG. 8), the pressure indicated by the gauge 27 corresponds to the intracavity pressure.

As has been explained above, the insufflation apparatus is a pulsed system including a plurality of discrete insufflation cycles, each of which consists of a filling phase Tp and an interruption phase Ti, as is indicated in FIGS. 1 and 5–11. The interruption phase represents an interval during which the flow transducer 22 generates a signal corresponding to 0 as a result of closing of the valve 18. As a consequence, insufflation $P_{ins}$ and intracavity $P_{abd}$ pressures are assumed to be equal thereby allowing the output signal of the pressure transducer 26 to represent the intracavity pressure $P_{abd}$, as is illustrated in FIGS. 5–7 and 10–12.

The pressure regulator 18, cut-off valve 20, flow transducer 22 and pressure transducer 26 are all connected to the control processing unit or CPU 6. A controller 28 of the control system evaluates the signals received from the transducers 22, 26 by comparing them with a nominal pressure $P_{nom}$, that is usually empirically available to an operator of the insufflator. Clearly, this nominal pressure is so selected that the flow rate of $CO_2$ does not exceed 2.5 l/min during a period of insufflation through the Veress needle. The controller 28 generates an electrical signal 30 opening the pressure regulator 18 so as to have the insufflator 2 cyclically operate in different modes depending on whether the measured flow rate and the insufflation pressure is higher or lower than a preset flow value and the nominal pressure, respectively. The electrical signal 30 is preferably a current signal i. However, a voltage signal can be used as well.

Figure 15:
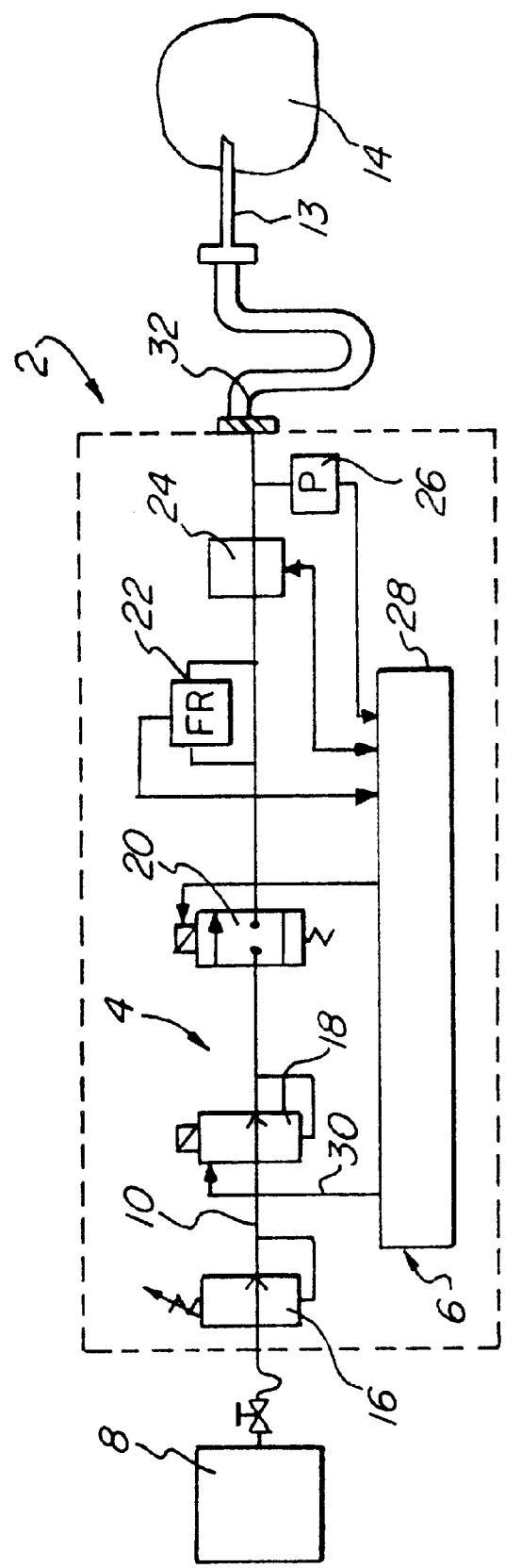
FIG. 15 is a schematic block diagram of a portion of an insufflation apparatus of the invention similar to FIG. 2, but with the needle replaced with a trocar.

Referring to FIGS. 2 and 3, the laparoscopic insufflator 2 operates in the following manner. To establish a pneumoperitoneum, the abdominal wall is punctured by the Veress needle 12 and verification of its correct positioning in the open abdominal cavity, an insufflation hose 32 is affixed to the needle 12 and the gas line 10 is ready for insufflation of the cavity. Since the internal diameter of the Veress needle limits the flow of pressurized fluid below 3 l/min, based on empirical data for penetration of the pneumo-peritoneum, a nominal pressure $P_{nom}$ is recommended to be 15 mmHg at the start of the insufflation cycle Tc. This nominal pressure along with the Veress needle's internal diameter of about 1 to 2 mm provides the gas flow that does not exceed 2 to 2.5 l/min, which is close to the value of 1 l/min recommended in the literature. Once the abdominal cavity is inflated at the nominal pressure, the needle is replaced by at least one trocar 13 (see FIG. 15) capable to be traversed by the fluid pressurized at approximately 30 mmHg and further, upon removing the trocar; the laparoscope is introduced through the trocar cannula.

Figure 4:
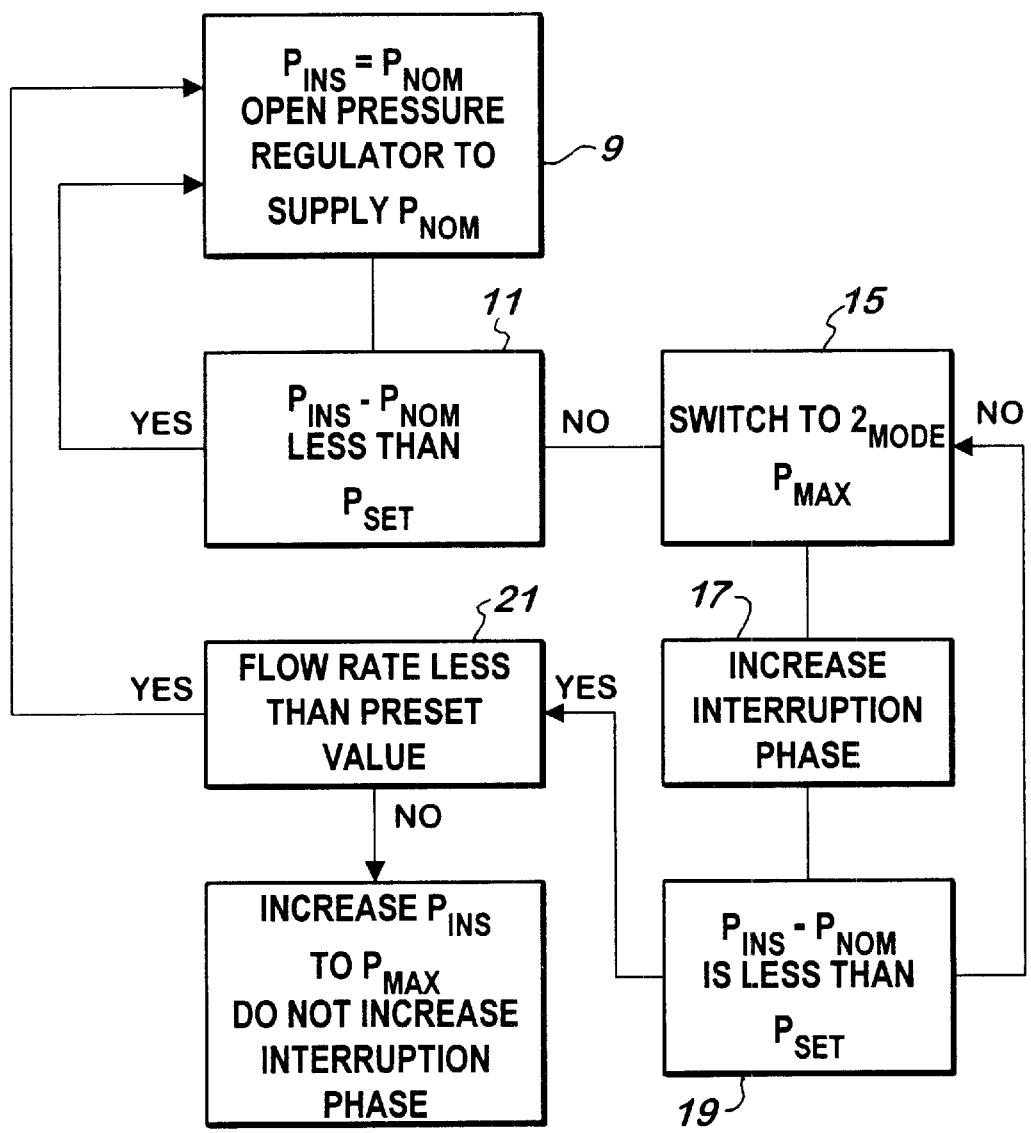
FIG. 4 is a flow chart illustrating a process of operating the insufflation apparatus of FIG. 2 according to one aspect of the invention.

As better illustrated in FIG. 4, the pressure transducer 26 continually monitoring the insufflation pressure $P_{ins}$ generates a signal that is evaluated by a comparator 32 of the controller 28 during an interruption or measurement phase $T_I$ upon expiration of a filling phase. If the signal $P_{ins}-P_{nom} \leq 10$ mmHg, which is a pre-set limit value, the controller generates a first output pilot signal $I_{min}$ that, due to a standard feed back block, controls opening of the pressure regulator 18 that sets a minimum target value $P_{min} \approx P_{nom}$. As a consequence, the insufflator operates in the first mode, which is characterized by the nominal pressure $P_{nom}$ controllably maintained upstream of the Veress needle 12 during the filling phase of each pulse.

Continuing to follow the flow rate gage 23 and the pressure gage 27, an operator is able to immediately detect an obstruction encountered by the Veress needle that manifests itself by a sharp drop of the rate and a sharp increase of the pressure, respectively. The CPU evaluating the received data, switches the continuously adjustable pressure regulator 18 to a second mode if $P_{ins}-P_{nom} > 10$ mmHg. Once the apparatus detects this encounter, it increases, for example, doubles the interruption phase, so that a volume of pressurized fluid accumulated upstream from the needle substantially dissipates therethrough. Only at the end of this increased interruption phase a measurement of the intracavity pressure is made. The fact that the measured pressure can be a little higher than the actual pressure in the cavity is acceptable. It has been empirically shown that during laparoscopy intra-abdominal pressures should not exceed 30 mmHg. However, if electronic pressure regulation fails, the possible pressure increase within a certain range above that maximum intracavity pressure is still acceptable in the short term. Thus, even if the insufflation pressure $P_{ins}$ upstream of the needle is increased above the empirically established safe value for a short time during laparoscopy, the patient will not experience any threatening consequences for some time. As a result, only at the end of the interruption phase the value for the digital display of the rate and the bar graph for pressure will be updated.

Referring to FIG. 4, if the needle does not encounter an obstruction, a difference between the measured pressure and a nominal pressure, as evaluated by the CPU, does not exceed a preset pressure value that is also indicated by gages 23 and 27. The continuously adjustable pressure regulator 18 controlled by the CPU 6 provides the gas line with the nominal insufflation pressure at 9 and the interruption phase lasts for a preset period of time if no obstruction is encountered.

If, however, the needle has encountered an obstruction at 11 as indicated the difference $P_{ins}-P_{nom}>10$ mmHg, the CPU switches the apparatus to its second mode by opening the pressure regulator 18 at 15 to provide a maximum 50 mmHg $P_{max}$ pressure sufficient to eliminate the obstruction.

As has been explained above, the increased internal apparatus pressure causes an increase of a dead volume upstream from the needle. To allow this volume to decay, the CPU keeps the pressure regulator closed for an increased interruption phase $T_I$ at 7, at the end of which $P_{abd}$ can be correctly measured at 19. During the next cycle, if the condition persists, the apparatus can continue to operate in the second mode. Upon overcoming the obstruction, the CPU having calculated that the difference $P_{ins}-P_{nom}<10$ mmHg generates a current signal that through a feed back circuit operates the pressure regulator to supply the insufflation pressure at the nominal value.

Figure 5:
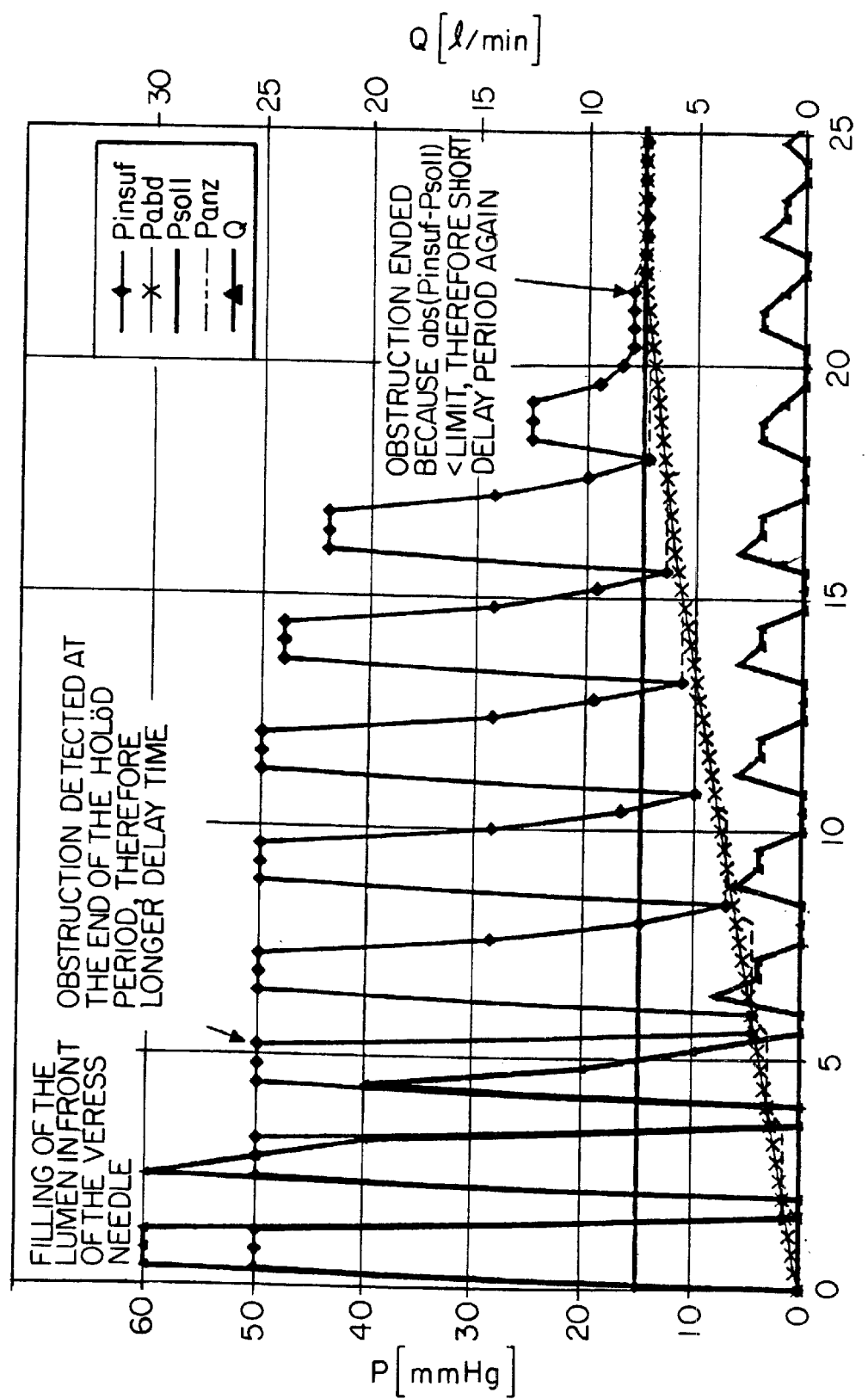
FIG. 5 is a timing diagram illustrating first and second modes of operation of the apparatus, wherein an interruption phase of an insufflation cycle in the second mode is increased relative to the same phase of the first mode.

FIG. 5 graphically illustrates a sequence of operations discussed above. Particularly, during a few initial cycles lasting, for example, first 5 seconds, the large volume of the apparatus upstream from the Veress needle is filled. There is a high flow Q and a large difference between the insufflation pressure of the apparatus and the nominal pressure. Since having the pressure elevated above 50 mmHg does not allow the apparatus to detect any obstruction, the apparatus works in the first mode. However, at the end of one of the initial cycles, approximately at 7.2 seconds, as shown in the diagram, the gas flow has subsided, and the apparatus, upon detecting that $P_{ins}-P_{nom}$ is more than 10 mmHg, is unequivocally able to indicate the encounter with obstruction. As a result, the interruption phase $T_i$ is extended to 0.8 seconds, which is twice as long as the interruption phases during previous cycles. Following this procedure, the operator knows the intracavity pressure $P_{abd}$ can be gradually brought to the nominal pressure $P_{nom}$ of 15 mmHg without unnecessary fluctuations, and the apparatus may be automatically switched back to the first mode characterized by the 0.4 sec interruption phase $T_i$.

Figure 6:
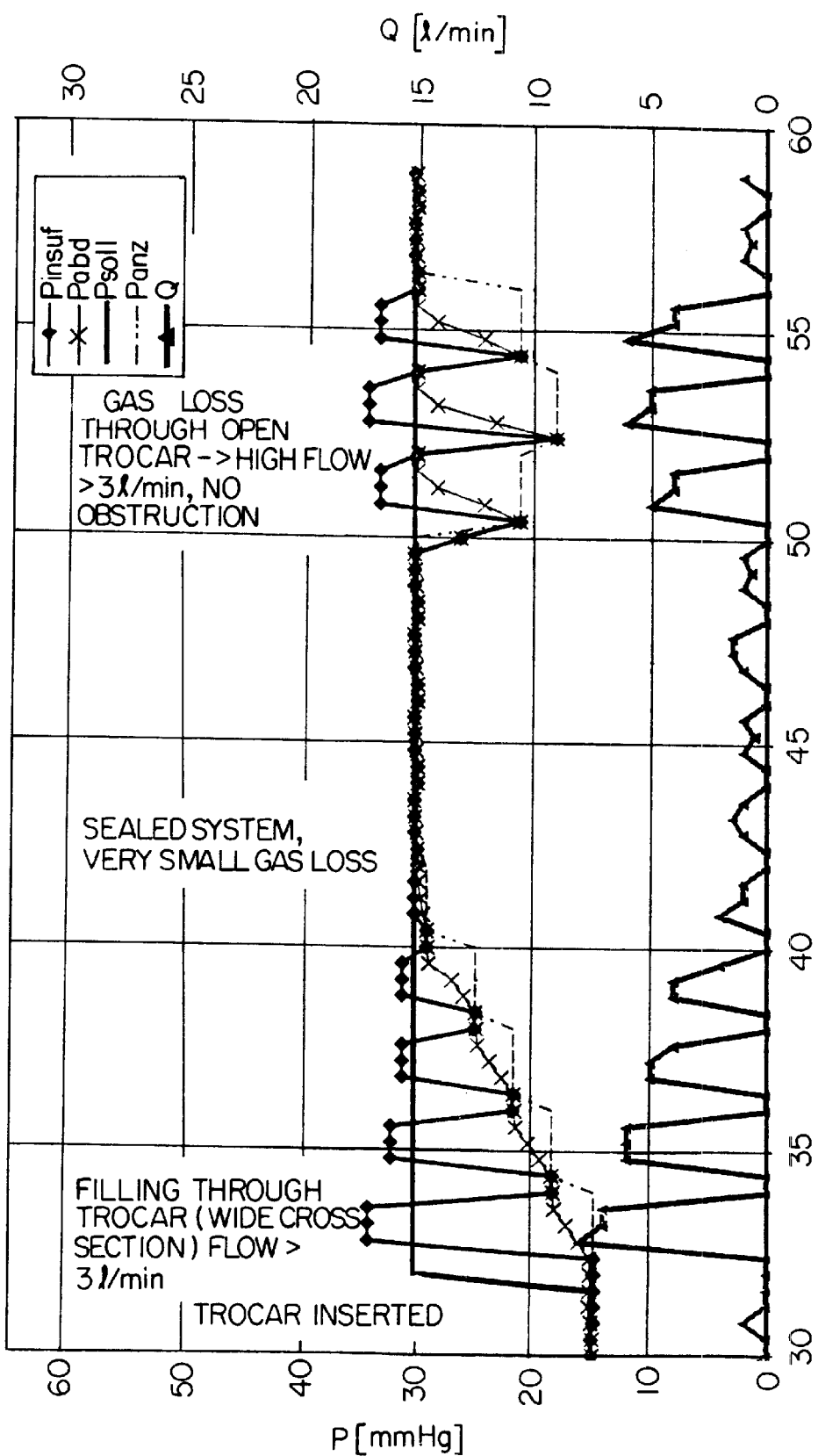
FIG. 6 is a timing diagram illustrating first and third modes of operation of the apparatus, wherein only an insufflation pressure is increased in the third mode while the interruption phase of the third and first modes are identical.
Figure 7:
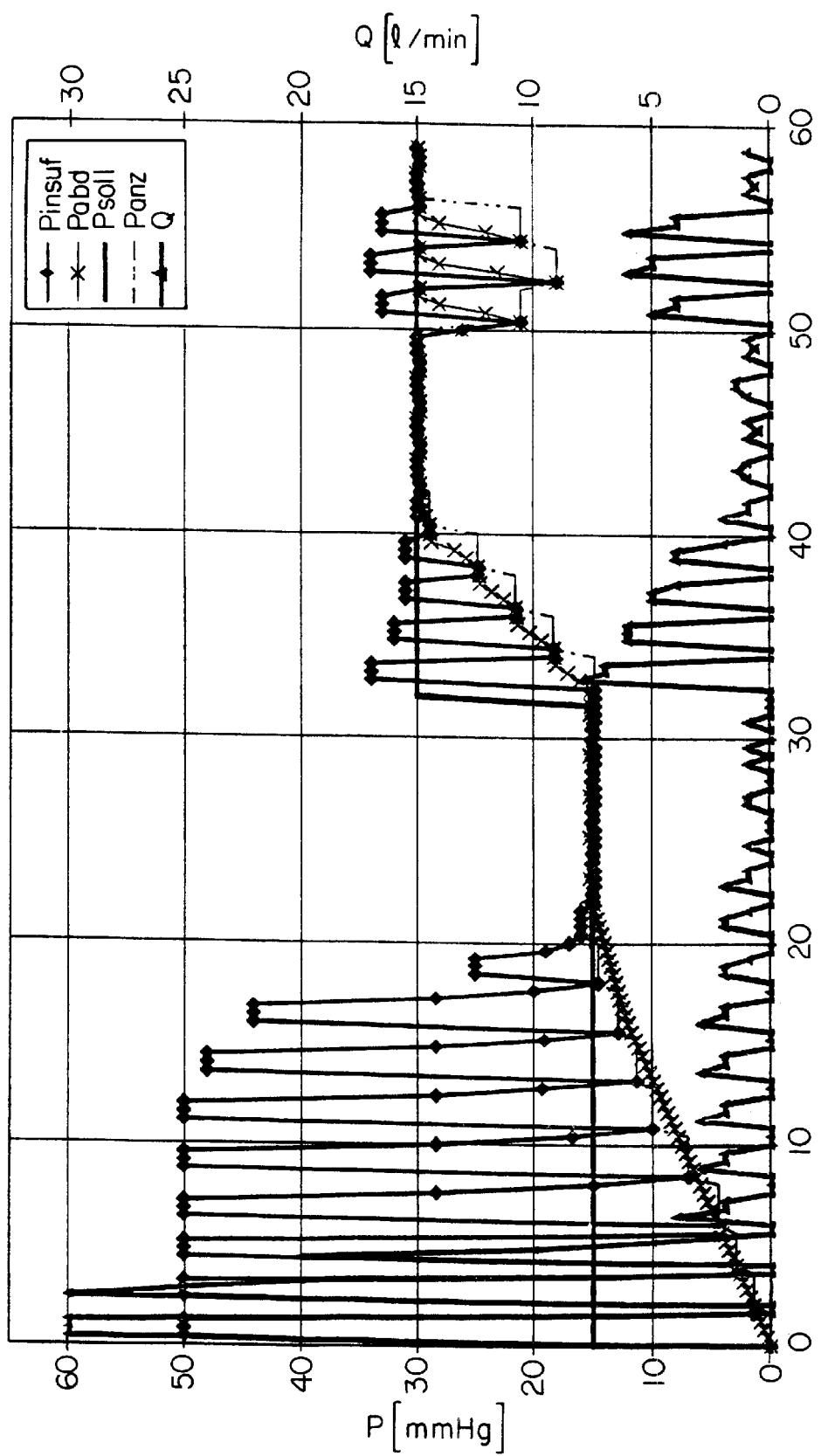
FIG. 7 is a timing diagram combining both diagrams illustrated in FIGS. 5 and 6.
Figure 8:
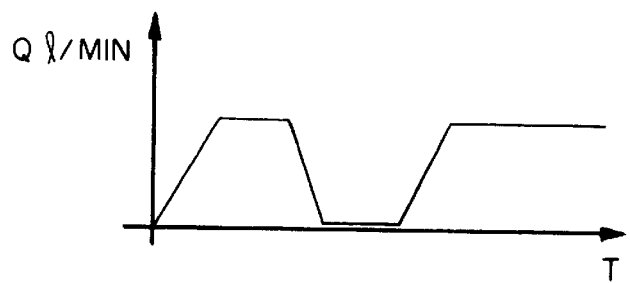
FIG. 8 is a timing diagram illustrating a flow rate of pressurized fluid during the first and second modes of FIGS. 5–7.
Figure 9:
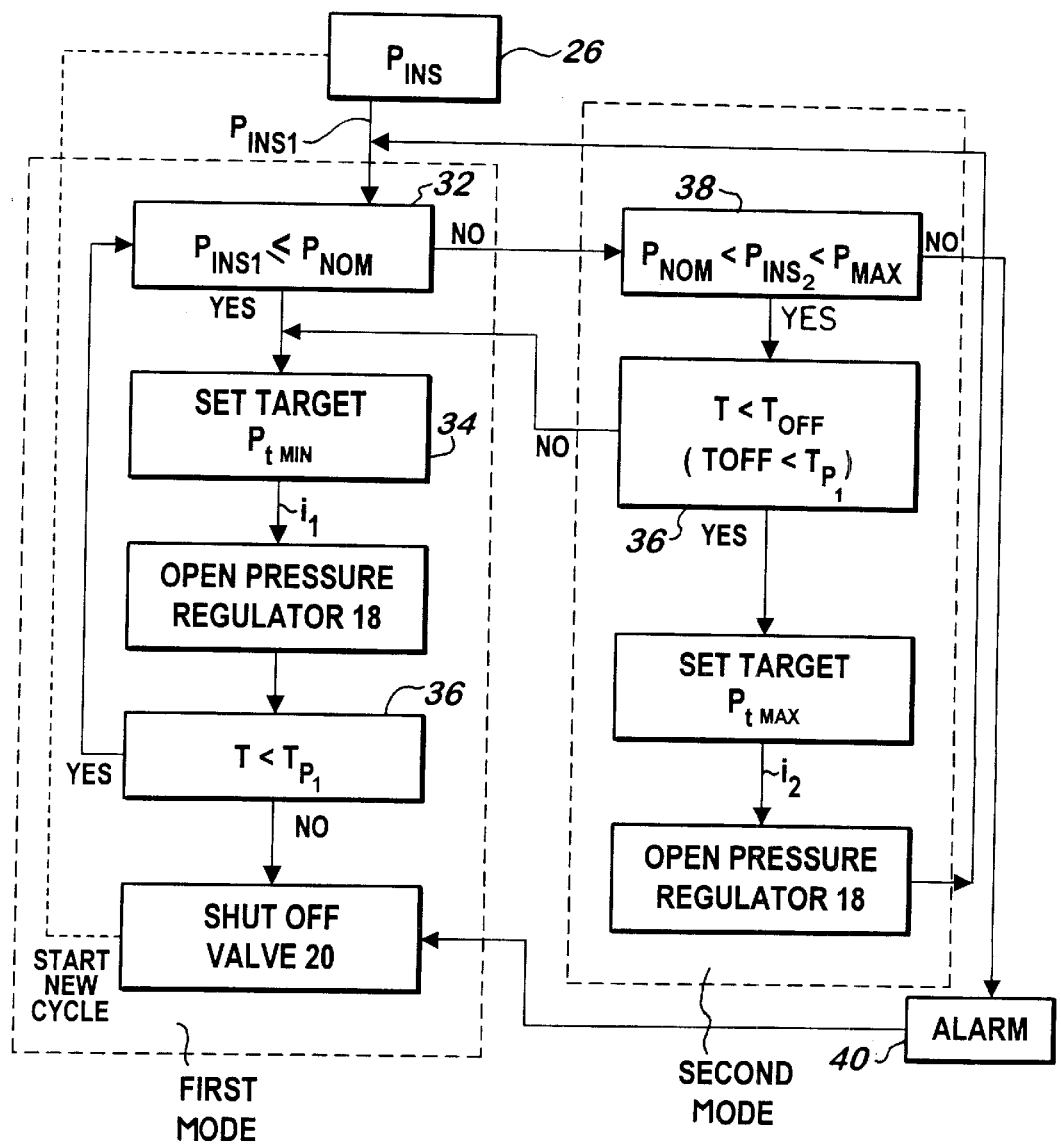
FIG. 9 is a flow chart of another embodiment of an apparatus shown in FIGS. 2–3.

A time diagram shown in FIG. 6 illustrates another aspect of the invention, according to which, the intracavity $P_{abd}$ has reached the nominal pressure $P_{nom}$. During next 10 seconds no obstruction is detected and the difference $P_{ins}-P_{nom}$ is practically non-existent. Later, at 30 seconds, a trocar having large inner dimensions is introduced into the inflated cavity and further insufflation is done through it at a higher working pressure of 30 mmHg. If during this stage of operation the flow rate is sharply increased above 3 l/min while the intra-abdominal pressure remains acceptable, then a system has developed a leakage and therefore the insufflation pressure has dropped, as indicated at 50 seconds. Since the difference $P_{ins}-P_{nom}$ is less than 10 mmHg, as seen in the diagram, the apparatus does not increase the interruption phase $T_i$ but increases the insufflation pressure $P_{ins}$. Thus, the two conditions for detecting the obstruction never arise together. FIG. 8 simply illustrates both aspects of the above-explained process.

According to another embodiment of the invention, the insufflator is able to operate in two modes, as explained above, without, however, increasing the total time of the insufflation cycle. Referring to FIGS. 2 and 9–12, while controlling the insufflation pressure $P_{ins}$, a timer 36 of the controller 28 keeps track of discreet time intervals of the insufflation pulse $T_{p1}$, so as to determine whether the measurement is made during a time interval $T_{off\ of}$ the pulse $T_{p1}$ for the reasons that will be explained hereinbelow.

This cyclical measurement of the insufflation pressure lasts until a measurement is taken at a time exceeding the pulse or filling phase $T_{p1}$, at which point the control system generates a signal activating the valve 18, interrupting the flow of fluid to the Veress needle 12. The stoppage determines the start of an interruption phase $T_i$ of the insufflation cycle $T_c$ during which zero gas flow is detected by the flow rate transducer 22, so as the pressure transducer 26 generates a signal corresponding to the intracavity pressure $P_{abd}$.

As has been explained above, although the flow rate upstream of the Veress needle is indicated to be zero upon closing the pressure regulator 18, the dead volume of fluid is accumulated at the upstream end of the Veress needle 12 for various reasons. This dead volume manifests itself by the undetected fluid flow through the needle affecting the accuracy of the measurement taken during the interruption phase. To ensure that at the time of measurement, no flow is present in the needle as a consequence of the dead volume, the controller 28 is programmed to increase the interruption phase of the insufflation pulse. This alone would result, however, in a perceptible reduction of the average gas flow, and this would be especially disturbing at high flow rates (Flow Rate/$T_c$) because of the increased overall time required to complete the insufflation during the operation. This prolonged overall surgical time increases the risk to a patient.

To avoid this risk and to maintain the constant cycle time $T_c$ in accordance with the invention, the controller 28 is programmed to operate in a second mode, wherein the interruption phase is increased to $T_{i2}>T_{i1}$, but the filling phase $T_{p2}$ is decreased. To complete the inventive concept, it is necessary to recognize whether an attempt to modify the interruption phase $T_i$ is made during penetration of various obstructions by the Veress needle during the operation.

Clearly, during penetration through an obstacle, the pressure transducer 26 generates a signal $P_{ins2}$ which is substantially stronger than the $P_{ins1}$ taken during the first mode of operation, whereas the flow transducer 22 generates a signal substantially weaker than a flow rate signal during the first mode. If this signal $P_{ins2}$ is also stronger than the nominal value $P_{nom}$ at a predetermined value, as evaluated by an evaluator 38, there is a strong indication of the needle's encounter with an obstacle.

As a result, the controller is ready to implement the second mode characterized by a reduced filling phase $T_{p2}$ and an increased target value $P_{tmax}$ that boosts the insufflation pressure upstream of the needle 12 such that this new pressure is sufficient to overcome the obstacle. This increased target value $P_{tmax}$ is set by the pressure regulator 18 actuated in response to an output electrical signal $I_{max}$ that is greater than the signal $I_{min}$ of the first mode.

As mentioned above, a temporary increase of intracavity pressure is still acceptable in the short term. Based on this available pressure increase, adjustment of the insufflation pressure to the maximum target value $P_{tmax}$ during the filling phase $T_{p2}$ allows it to realize the second mode of operation according to the invention without jeopardizing the patient's health.

However, before implementing this second mode, the timer 36 determines a time of the filling phase $T_{p1}$ at which the measured pressure, indicating the presence of an obstacle, exceeds the nominal pressure. If this event occurs within a predetermined time portion $T_{off}<T_{p1}$ of the filling phase during the first mode, then the controller will switch the insufflation apparatus to the second mode. Otherwise, if the obstruction is detected during the $T_{p1}-T_{off}$ interval, the apparatus remains in the first mode of operation for the following reason.

Upon switching to the second mode, the insufflation pressure $P_{ins}$ upstream of the Veress needle fluctuates about this new maximum value $P_{tmax}$. Since the Veress needle limits the flow, the dead volume at its upstream end resulting from the increased pressure is greater than it is under normal conditions. As a result, it needs greater decay time for dissipating through the needle 12 than the decay time during the first mode. This decay time in the second mode may both substantially stretch beyond the interruption phase of the second mode that has not been sufficiently increased and cause a significant error.

However, if the insufflation apparatus 2 still remains in the first mode characterized by the minimum target value $P_{tmin}$ it does not substantially contribute to increase in the dead volume which is accumulated at an upstream end of the needle as a consequence of the encounter with an obstacle. Thus, despite a possibility of stretching the decay time beyond the start of the next cycle in the first mode, a resulting error can be relatively insignificant and can be easily corrected during subsequent insufflation cycles.

If an obstruction, however, has been detected during the first mode but before the predetermined time $T_{off}$, the second mode is activated by generating the current signal $I_{max}$. The pressure regulator 18 responding to this new current signal opens such that the insufflation pressure $P_{ins}$ is increased to a maximum target value $P_{tmax}$ and is maintained as long as the condition indicating the presence of an obstacle persists.

The insufflation apparatus 2 may also operate in an alarm mode shown in FIG. 4 and corresponding to the signal $P_{ins2}$ that substantially exceeds the maximum safe insufflation pressure $P_{max}$ which, as mentioned before, is 50 mmHg. In this mode, sound and visual alarm 40 may be activated and the cycle will be immediately terminated. If, however, the insufflation pressure is within an acceptable range above $P_{max}$, it is possible to use the relief valve 24 (FIG. 2) without interrupting the insufflation cycle.

Turning to FIGS. 10 and 11, the method operating the apparatus according to the invention is illustrated. Particularly, FIG. 10a shows the first mode, wherein the controller 28 generates a plurality of discreet output signals $I_{min}$ during the filling phase $T_{p1}$ followed by an interruption phase $T_{i1}$. A sum of $T_{p1}$ and $T_{i1}$, which is an interval between subsequent pulses, corresponds to the total time of the insufflation cycle Tc.

Figure 10A:
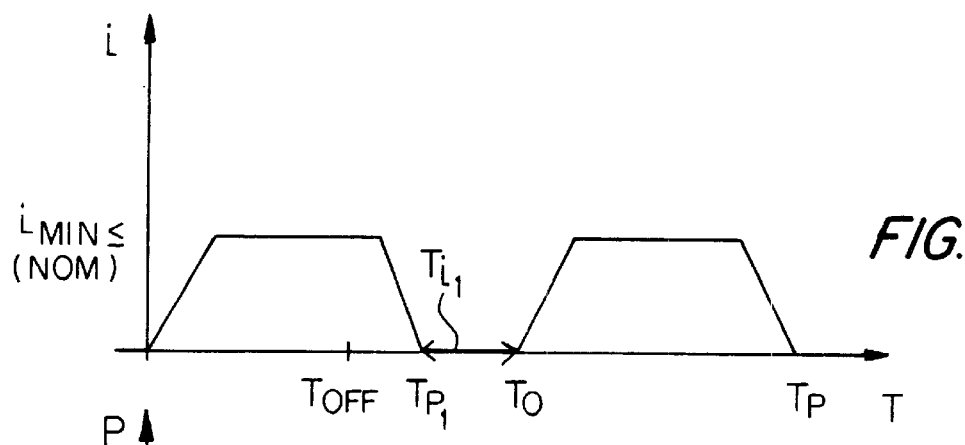
FIG. 10a is a timing diagram illustrating an output signal generated by a controller of the insufflation apparatus working in its first mode of operation corresponding to an unobstructed penetration of a Veress needle into a body cavity in accordance with the invention.
Figure 10B:
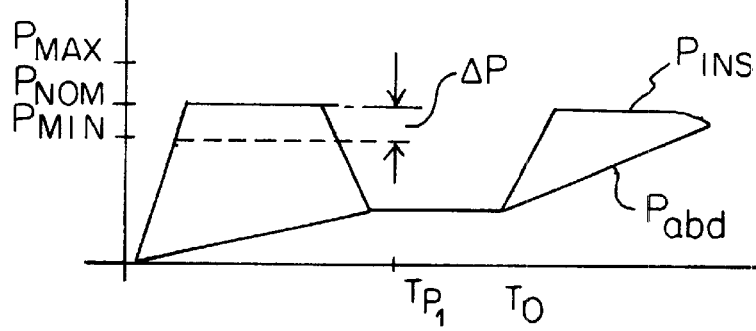
FIG. 10b is timing diagram illustrating an insufflation pressure upstream of a Veress needle of the insufflation apparatus during an insufflation cycle and a pressure in a body cavity in response to the output signal of FIG. 10a in the first mode of operation.

As shown in FIG. 10b, in response to the signal $I_{min}$, the pressure regulator 18 opens to maintain the insufflation pressure $P_{ins}$ within a predetermined range $\Delta P$ of the minimum target value $P_{tmin}$. This minimum target value is selected so as to have the fluid flow upstream of the Veress needle to be at most equal to 2.5 l/min. The intracavity pressure $P_{abd}$ tends to reach the target value within a certain period of time which is a function of the target value, the needle's cross section, a number of components etc. In the illustrated example, the target value is reached during two cycles.

As is explained above, because the pressure transducer 26 is typically placed upstream of the Veress needle 12, the correct reading of the intracavity pressure $P_{abd}$ occurs only during the interruption phase $T_i$ corresponding to the zero flow rate through the needle upon closing the pressure regulator 18. This is illustrated in FIG. 10c.

Figure 10C:
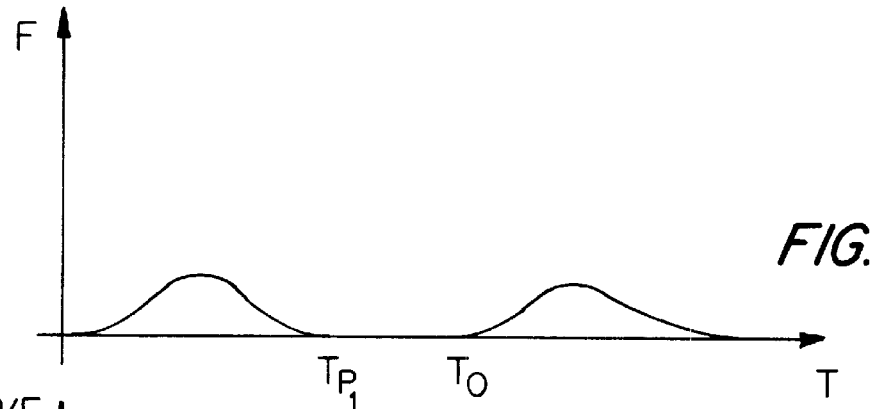
FIG. 10c is a timing diagram illustrating a rate of flow of a pressurized fluid through a Veress needle in the first mode of operation of the insufflation apparatus according to the invention.
Figure 10D:
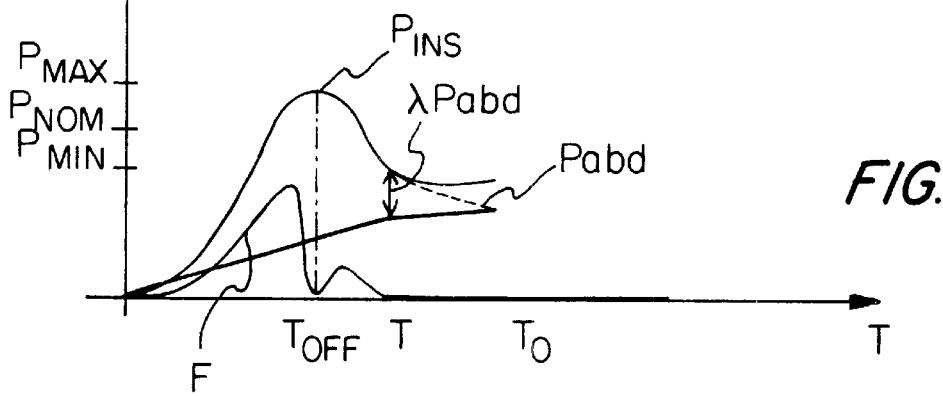
FIG. 10d is a timing diagram illustrating an increase in the insufflation pressure in response to encountering an obstruction by a Veress needle during a filling phase or pulse of an insufflation cycle in the first mode of operation.

Under normal conditions illustrated in FIGS. 10b and 10c, the dead volume of the pressurized fluid accumulated at the upstream end of the Veress needle decays during a relatively short period of time upon termination of the filling phase $T_{p1}$. The measurements of the intracavity pressure $P_{abd}$ made during the interruption phase $T_{i1}$ adequately correspond to its actual values.

FIG. 5d illustrates an encounter of the Veress needle with an obstruction that, as discussed above, manifests itself by a precipitous increase in the pressure upstream of the needle 12 and an abrupt decrease of the flow rate. The solid line of the flow graph indicates that at the time of termination of the filling phase $T_{p1}$ the flow rate transducer generates a signal corresponding to 0. However, a dash line of this graph indicates the presence of flow through the needle during the interruption phase, as has been explained above. The increased pressure causes expansion of the dead volume that requires the decay period corresponding to the undetected flow greater than such period under conditions of FIGS. 10b–10c. As a result, the margin of error in measurements during the interruption phase $T_{i1}$ varies from $\lambda P_{abd1}$ to $\lambda P_{abd2}$.

FIG. 11 illustrates the second mode of operation of the insufflation apparatus directed to allow the increased dead volume of FIG. 5d to decay during an increased interruption phase $T_{i2}$ of the cycle $T_c$ during which an encounter has occurred.

Figure 11A:
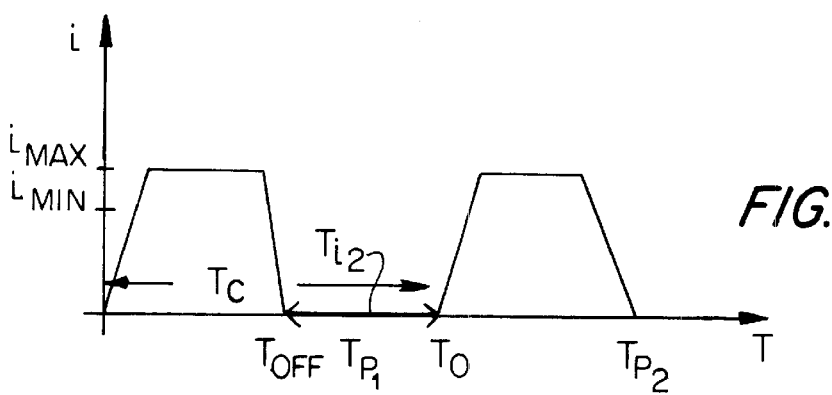
FIG. 11a is a timing diagram illustrating an electrical output signal of a controller of the insufflation apparatus according to its second mode of operation upon detecting an obstruction encountered by a Veress needle.

As shown in FIG. 11a, in response to the signal $P_{ins2}$ from the pressure transducer 26 indicating the presence of an obstruction, the controller 28 generates the current signal $I_{max}$, which is greater than the current signal of the first mode. As a consequence, the pressure regulator 18 is open to maintain the required flow rate with the new maximum target value $P_{max}$. However, this new signal $I_{max}$ is shorter than the current signal $I_{min}$ so as to have the relatively short filling phase $T_{p2}$ and the relatively long interruption phase $T_{i2}$ which, combined together, amount to the total time of pulse Tc of the first mode.

Figure 11B:
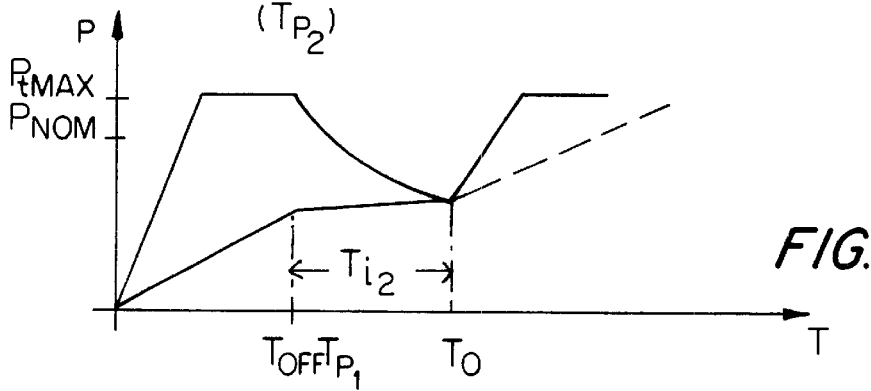
FIG. 11b is a timing diagram illustrating an insufflation pressure upstream of a Veress needle during an insufflation cycle and a pressure in a body cavity in response to the output signal of FIG. 6a according to the second mode of operation of the insufflation apparatus.
Figure 11C:
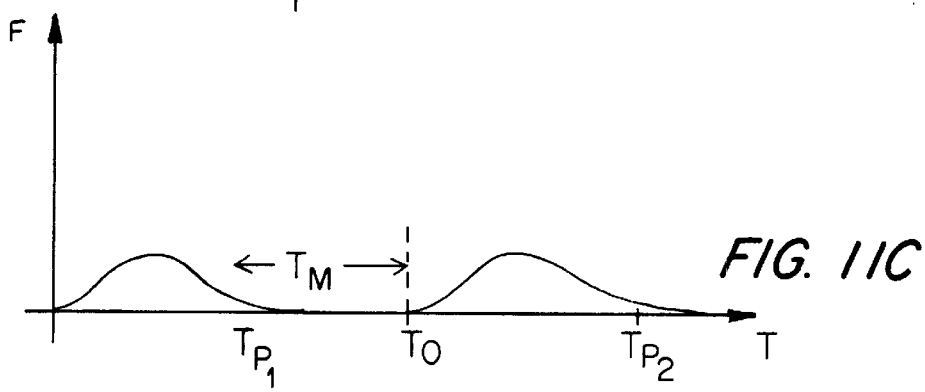
FIG. 11c is a timing diagram illustrating a rate of flow of a pressurized fluid through a Veress needle of the insufflation apparatus in its second mode of operation.

FIG. 11c illustrates the flow terminating approximately at the same time $T_{p1}$ as the one shown in FIG. 10c. Thus, these measurements, as shown in FIG. 11b and taken upon termination of the flow through the needle in accordance with the inventive apparatus, indicate actual values of the intracavity pressure and, as a result, the safety problem of incorrect measurements is overcome.

Figure 12:
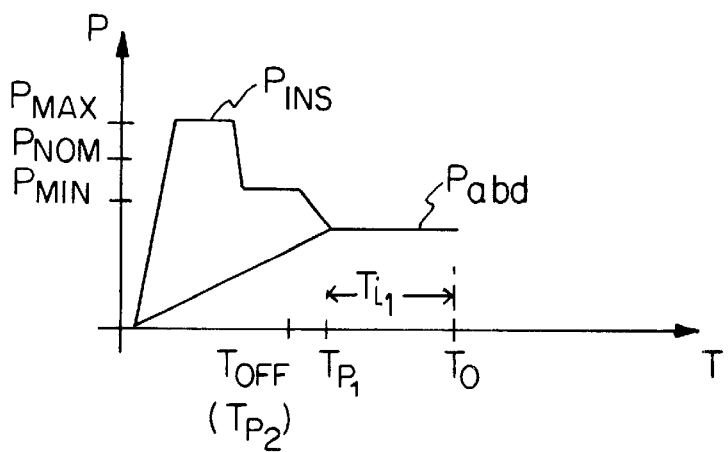
FIG. 12 is a timing diagram illustrating another mode of operation of an insufflation apparatus according to the invention.

FIG. 12 illustrates another aspect of the present invention corresponding to a switching mode of operation of the controller 28, wherein, upon overcoming the obstruction, the insufflation apparatus 2 is returned to the first mode of operation.

Turning to FIGS. 13–14, the invention discloses two systems of the controller 28 providing this switching from the second mode of the insufflation apparatus 2 to its first one. Specifically, FIG. 13 illustrates the system operating on a basis of determining the rate of pressure built up during the second mode by implementing, for instance, a differentiator 42. Further, utilizing an averaging circuit 44, it is possible to determine the average built up rate during the second mode and, then, to compare it with the average built up rate of the first mode by using a comparator 46. If the rates are comparable, the insufflator 2 is returned to the first mode of operation. If, however, the rate during the second mode is still greater than the one of the first mode, then the insufflator continues to work in the second mode as long as the obstruction blocks the needle.

FIG. 14 illustrates another system whose operation is based on a signal representing the flow rate change determined by a differentiator 52 during the second mode of operation of the insufflator 2. An averaging circuit 54 determines the average flow rate, and a comparator 56 evaluates the average rates of the first and second modes so as to enable the insufflator either to continue the second mode or to activate the first one.

It is apparent that many modifications and variations of the present invention are possible in light of the above teaching including the controller 28 that may be a computerized system or a circuitry consisting of semi-conductors. It is, therefore, to be understood that, within the scope of the appended claims, the invention may be practiced otherwise as specifically described.

What is claimed is:

1. An apparatus for controlling the flow of pressurized fluid inflating a body cavity in a pulsed insufflation system, wherein each pulse is characterized by a filling and interruption phase, comprising:

a source of pressurized fluid flowing along a path;

a needle in flow communication with the source and the body cavity;

a continuously adjustable pressure regulator along the path between the source and the needle for selectively supplying a nominal pressure $P_{nom}$ and a maximum pressure $P_{max}$, which is greater than the nominal pressure ($P_{max} > P_{nom}$);

a controller for measuring a pressure of pressurized fluid $P_{ins}$ delivered through the needle and having a central processing unit with a program executing thereon for switching the pressure regulator between first and second modes, the program switching the pressure regulator to the first mode to supply a nominal pressure in response to a first signal generated by the controller and representing a difference between measured and nominal pressures to be at most equal to a preset pressure value $P_{set}$ ($P_{ins} - P_{nom} \leq P_{set}$), the program switching the pressure regulator to the second mode to supply $P_{max}$ in response to a second signal signifying encounter of the needle with an obstruction and representing the difference between the measured and nominal pressures to be greater than the preset pressure value ($P_{ins} - P_{nom} > P_{set}$), the interruption phase of the insufflation cycle in the second mode being longer than that one of the first mode, so as to allow a volume of the pressurized fluid accumulated upstream from the needle to decay through it, thereby accurately measuring an intra-cavity pressure $P_{abd}$ at the end of this interruption phase.

2. The apparatus defined in claim 1 wherein the interruption and filling phase of the second mode combined constitute an insufflation cycle that is longer than an insufflation cycle of the first mode.

3. The apparatus defined in claim 1 wherein the interruption and filling phases of the second mode constitute an insufflation cycle that is equal to an insufflation cycle of the first mode.

4. The apparatus defined in claim 1 wherein the nominal pressure $P_{nom}$ is approximately 15 mmHg, the pre-set pressure $P_{set}$ is set about at 10 mmHg and said maximum pressure can reach above 50 mmHg.

5. The apparatus defined in claim 1 wherein the interruption phase of the second mode is approximately twice as long as the interruption phase of the first mode.

6. The apparatus defined in claim 1 wherein the central processing unit includes an evaluating circuit calculating the $P_{ins} - P_{nom}$ difference and a feedback circuit generating the signal switching the pressure regulator between the first and second modes in response to the evaluation of the difference.

7. The apparatus defined in claim 1 wherein the $P_{ins} - P_{nom}$ difference is calculated at the end of the filling phase.

8. The apparatus defined in claim 1 wherein the $P_{ins} - P_{nom}$ difference is calculated before the filling phase expires.

9. The apparatus defined in claim 1, further comprising flow and pressure located along the path of pressurized fluid and operatively connected to the central processing unit to generate signals representing gas flow and insufflation pressure.

10. The apparatus defined in claim 1 wherein the central processing unit further includes gages indicating the flow rate, insufflation pressure and a total volume of pressurized fluid used during inflation of the cavity, respectively.

11. An apparatus for controlling the flow of pressurized fluid inflating a body cavity in a pulsed insufflation system, wherein each pulse is characterized by a filling and interruption phase, comprising:

a source of pressurized fluid flowing along a path;

a puncturing instrument in flow communication with the source and the body cavity;

a continuously adjustable pressure regulator along the path between the source and the instrument;

a controller for measuring a pressure $P_{ins}$ of pressurized fluid delivered through the needle and having a central processing unit with a program executing thereon for operating in first, second and third modes, said pressure regulator being open to supply a nominal pressure $P_{nom}$ in the first mode and a maximum pressure $P_{max}$ in the second and third modes, the controller also evaluating a flow rate of the pressurized fluid and comparing it with a preset flow rate; and the program selectively switching the controller between the first and second modes, said program being normally applied in the first mode, said program switching the controller to the second mode upon detecting increase of the insufflation pressure in the needle above a pre-set pressure value $P_{set}$, wherein said second mode has an extended interruption phase relative to an interruption phase common to the first and third modes, so as to allow a volume of pressurized fluid accumulated upstream from the instrument to decay through it, the program switching the controller to the third mode upon detecting precipitous increase of a measured flow rate above the preset flow rate after the cavity has been inflated at an intra-cavity pressure $P_{abd}$ substantially equal to the nominal pressure, which is at least equal to the preset pressure value and less than the maximum pressure ($P_{set} \leq P_{nom} < P_{max}$), so as the controller enables the pressure regulator to supply the maximum pressure $P_{max}$ during the filling phase and to be shut down during the interruption phase in the third mode.

12. The apparatus defined in claim 11 wherein the puncturing instrument is selected from the group consisting of a Veress needle and a trocar, the trocar being traversed by the pressurized fluid upon inflating the cavity at the intra-cavity pressure $P_{abd}$ equal to 30 mmHg.

13. The apparatus defined in claim 12 wherein the preset flow rate is 3 l/min.

14. A method of controlling a pulsed insufflation system having a puncturing instrument adapted to be inserted in a body cavity, a source of pressurized medium connected to said puncturing instrument and a pressure controller between said source and said instrument, said method comprising the steps of:

(a) measuring an insufflation pressure of pressurized medium through a puncturing instrument having a relatively small cross-section during a filling phase of a cycle;

(b) comparing a measured insufflation pressure with a nominal insufflation pressure and generating a signal corresponding to a difference therebetween;

(c') either switching the pressure controller to a first mode of operation, wherein the nominal pressure is supplied in response to the signal indicating that the difference is at most equal to a preset pressure value, the pressure controller being shut down for a first interruption phase;

(c") switching the pressure controller to a second mode of operation, wherein the insufflation pressure is maintained at a maximum value in response to the signal indicating that the difference is greater than the preset pressure and subsequently shutting down the pressure controller for a second interruption phase, which is greater than the first one and sufficient to allow a dead volume of pressurized fluid to decay through the puncturing instrument, so as to have a correct measurement of the intra-cavity pressure; or (c''') switching the pressure controller to a third mode of operation, wherein the insufflation pressure is maintained at a maximum value in response to another signal indicating that a difference between a measured flow rate exceeds a preset flow rate upon inflating the cavity at the nominal pressure and, subsequently, shutting down the pressure controller for the interruption phase identical to the one of the first mode.

15. The apparatus defined in claim 14, further comprising a pressure reducer in flow communication with the source of pressurized fluid, the pressure reducer decreasing the pressure to 2 bars, and a pressure regulator connected in series with the pressure reducer.

16. The apparatus defined in claim 15 wherein the pressure regulator is controllably adjusted to regulate the pressure upstream of the needle between 0 to 50 mmHg.

17. The apparatus defined in claim 15 wherein the pressure regulator opens in response to a first electrical signal generated by the controller to maintain a minimal target value of the pressure in the apparatus.

18. The apparatus defined in claim 16 wherein the controller has a comparator comparing a signal corresponding to a nominal pressure with a signal corresponding to a measured pressure.

19. The apparatus defined in claim 18, further comprising a flow rate transducer generating a signal corresponding to a flow rate of the pressurized fluid in the apparatus.

20. The apparatus defined in claim 18 wherein the signal corresponding to the measured pressure is generated by a pressure transducer located upstream of the needle and electrically connected to the controller.

21. The apparatus defined in claim 16 wherein the pressure regulator opens in response to a second electrical signal generated by the controller when the signal representing the measured pressure exceeds the signal corresponding to the nominal pressure at a predetermined value.

22. The apparatus defined in claim 21 wherein said second signal corresponds to the maximum value of the pressure upstream of the needle.

23. The apparatus defined in claim 21 wherein the controller includes a timer controlling a predetermined portion of a filling phase and enabling the controller to generate the second signal in response to the pressure increase in the needle toward the maximum value upon detection of a precipitous increase in the measured pressure during the predetermined portion.

24. The apparatus defined in claim 23 wherein the controller generates the first signal in response to the pressure increase detected after the predetermined portion of the filling phase has expired.

25. The apparatus defined in claim 14 wherein the controller is further programmed to decrease the pressure of pressurized fluid in the needle toward the minimum value as a condition caused the precipitous increase has ceased.

26. A method of controlling a pulsed insufflation system having a needle adapted to be inserted in a body cavity, a source of pressurized medium connected to said needle and a pressure controller between said source and said needle, said method comprising the steps of:

(a) measuring an insufflation pressure of pressurized medium through a needle during a filling phase of a cycle;

(b) comparing a measured insufflation pressure with a nominal insufflation pressure;

(c) continuously adjusting the insufflation pressure toward a minimum target value thereof if a measured insufflation pressure is at most equal to the nominal insufflation pressure;

(d') either increasing the insufflation pressure toward a maximum target value thereof if a precipitous increase in the insufflation pressure has occurred during a predetermined portion of the filling phase, or (d') continuously adjusting the pressure toward the minimum target value if the precipitous increase has occurred beyond the predetermined portion;

(e) cyclically repeating steps (a)–(c).

27. The method defined in claim 26 wherein the step (c) of adjusting the pressure further includes the step of detecting the precipitous increase in the insufflation pressure of the pressurized fluid.

28. The method defined in claim 27 wherein the precipitous increase in the pressure above the nominal pressure at a predetermined value signifies an encounter between the needle and an obstruction.

29. The method defined in claim 27 wherein the step of detecting a precipitous increase of the pressure includes the step of detecting a sharp decrease in a flow rate of the pressurized fluid.

30. The method defined in claim wherein 27 wherein the insufflation pressure is measured by an electronic transducer generating an electrical signal.

31. The method defined in claim 26, further comprising the step of comparing the electrical signal corresponding to the measured insufflation pressure to a signal corresponding to the nominal insufflation pressure.

32. The method defined in claim 31, further comprising the step of generating a first electrical output signal if the electrical signal representing the measured insufflation pressure is less than the signal corresponding to the nominal insufflation pressure.

* * * * *